United States Patent [19]

Ashman

[11] 4,199,864
[45] Apr. 29, 1980

[54] ENDOSSEOUS PLASTIC IMPLANT METHOD

[76] Inventor: Arthur Ashman, 200 Central Park South, New York, N.Y. 10019

[21] Appl. No.: 854,031

[22] Filed: Nov. 22, 1977

Related U.S. Application Data

[62] Division of Ser. No. 643,405, Dec. 22, 1975, abandoned.

[51] Int. Cl.² ............................................. A61C 13/22
[52] U.S. Cl. ........................................ 433/175; 433/223
[58] Field of Search ........................ 32/10 A; 128/92 A

[56] References Cited

U.S. PATENT DOCUMENTS

| | | | |
|---|---|---|---|
| 3,589,011 | 6/1971 | Sneer | 32/10 A |
| 3,628,248 | 12/1971 | Kroder | 32/10 A |
| 3,672,058 | 6/1972 | Nikoghossian | 32/10 A |
| 3,790,507 | 2/1974 | Hodosh | 260/2.5 R |
| 3,808,606 | 5/1974 | Toronzo | 32/10 A |
| 3,827,145 | 8/1974 | Richards | 32/10 A |
| 3,829,972 | 8/1974 | Pasqualini et al. | 32/10 A |
| 3,849,888 | 11/1974 | Linkow | 32/10 A |
| 3,905,109 | 9/1975 | Cohen et al. | 32/10 A |
| 3,928,914 | 12/1975 | Kozlovsky | 32/10 A |
| 3,936,887 | 2/1976 | Hodosh | 32/10 A |
| 3,952,414 | 4/1976 | Shovers | 32/10 A |
| 3,971,134 | 7/1976 | Bokros | 32/10 A |
| 4,024,639 | 5/1977 | Weiss | 32/10 A |
| 4,051,598 | 10/1977 | Sneer | 32/10 A |

OTHER PUBLICATIONS

Catalog pages of Park Dental Research Corp., "Linkow Blade Vents", 19 West 34th Street, New York, N.Y. 10001.

*Primary Examiner*—Robert Peshock
*Attorney, Agent, or Firm*—Kenyon & Kenyon

[57] ABSTRACT

Nontoxic polymeric plastic medical implants for endosteal and periosteal applications such as filling bone defects, replacing entire bony parts, and tooth replacement either immediately after extraction or subsequent to healing, and a method of fabricating such implants to produce a porous surface having a predetermined pore size, pore depth, and degree of porosity. The method of fabrication of the porous portion of the implant involves adding sodium chloride crystals or other nontoxic leachable substance of controlled particle size corresponding to the desired pore size to a powdered polymer-liquid monomer mixture in relative amounts corresponding to the desired degree of porosity. After heat polymerization without an initiator, followed by abrasive removal of the resulting surface skin, the salt is leached from the plastic to provide said porosity. To obtain bone ingrowth in the case of intraosseous implantation, the pore size must be 200–400 microns, whereas pore size for soft tissue ingrowth should be 50–150 microns.

30 Claims, 61 Drawing Figures

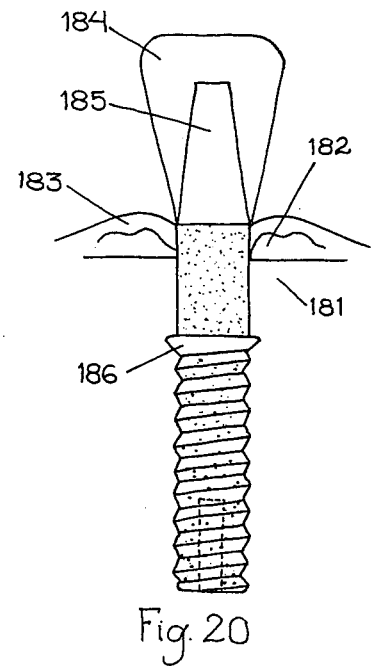
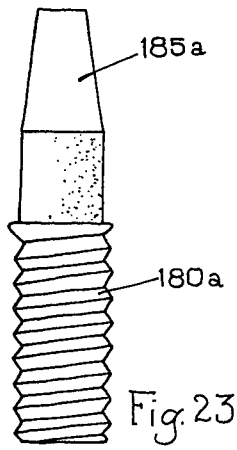
Fig. 23A
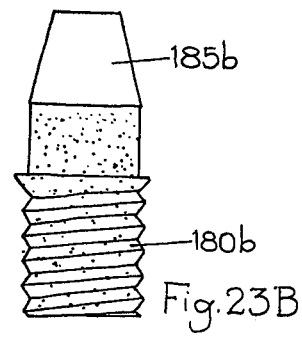
Fig. 23B
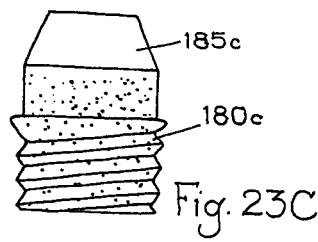
Fig. 23C
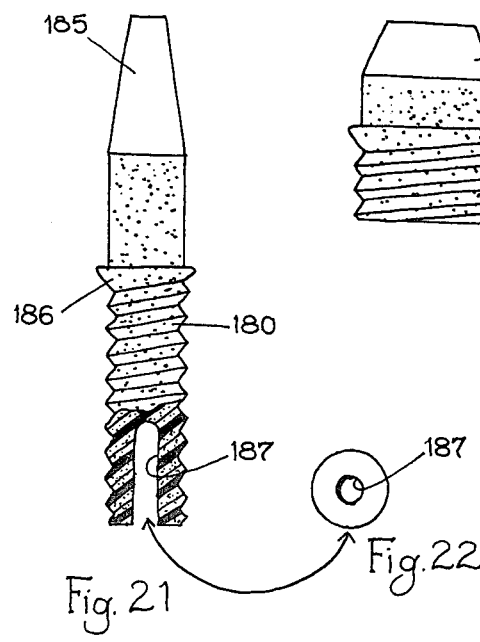
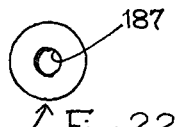
Fig. 21
Fig. 22
Fig. 20

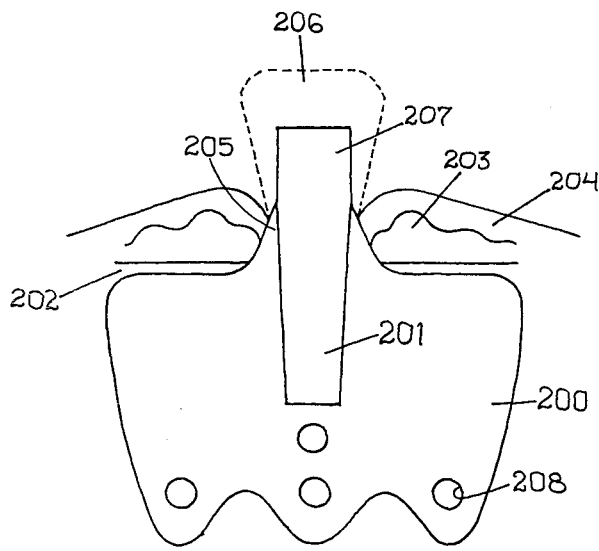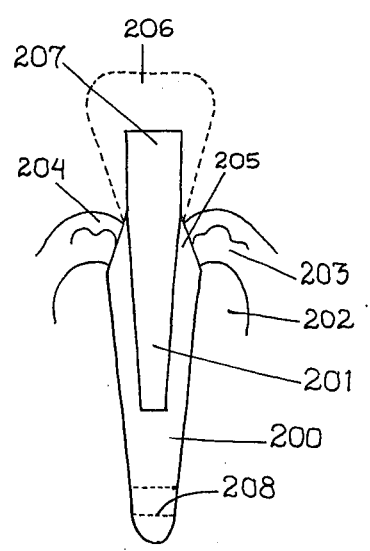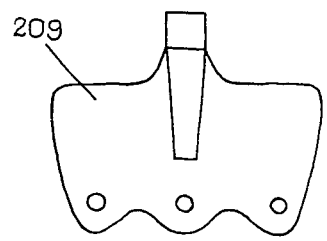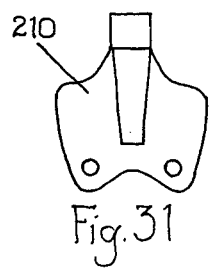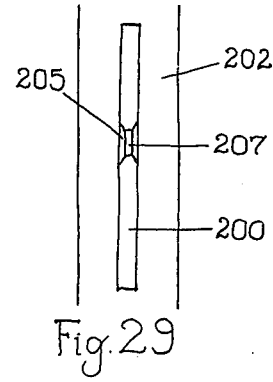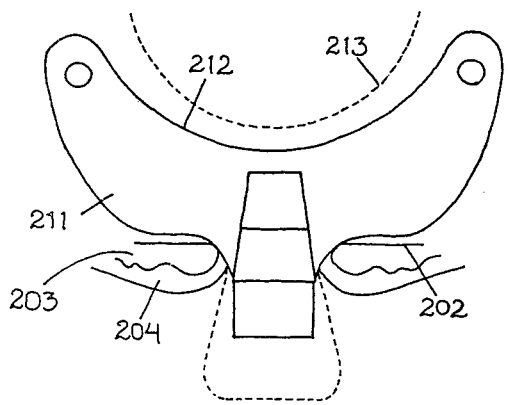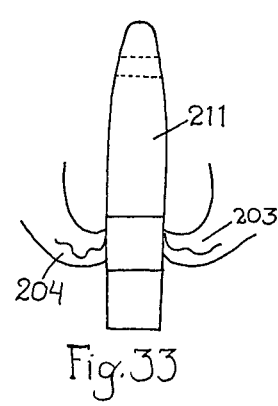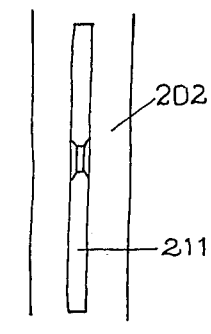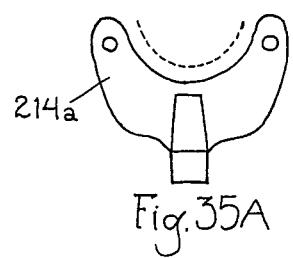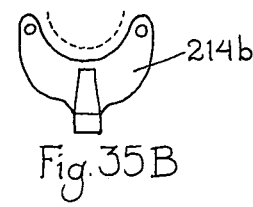

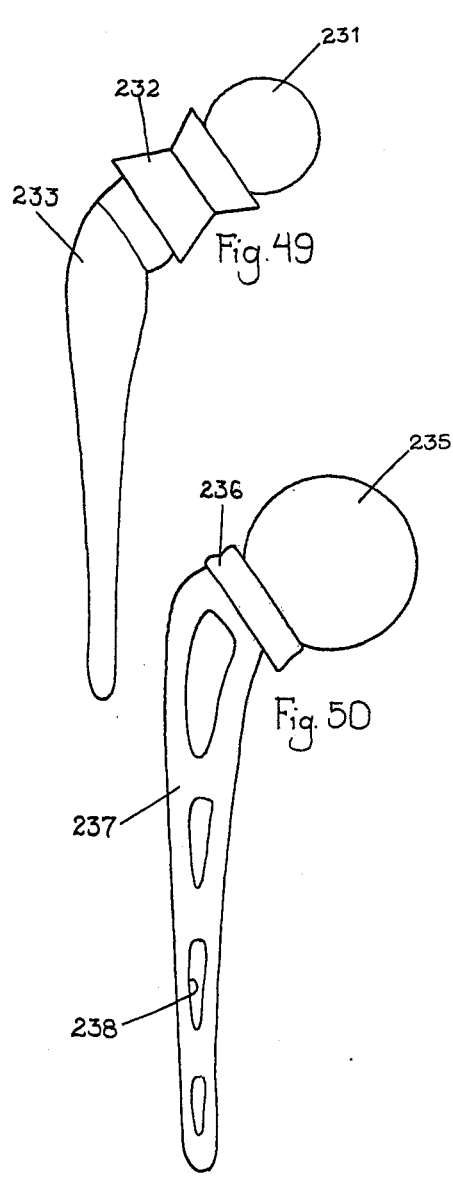
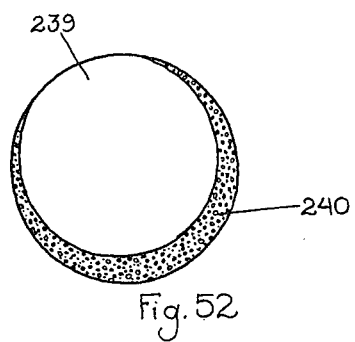
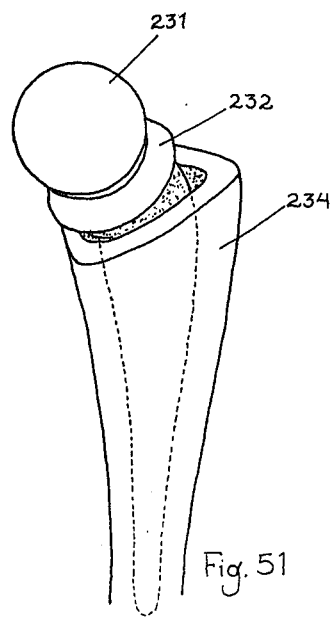

ENDOSSEOUS PLASTIC IMPLANT METHOD

This is a division of application Ser. No. 643,405 filed Dec. 22, 1975, and now abandoned.

BACKGROUND OF THE INVENTION

The present invention relates to prosthesis materials for artificial bones or teeth and particularly to a plastic implant and a method for fabricating such a plastic implant to have a controlled surface porosity, with pore size depending upon the nature of tissue ingrowth desired.

In the related fields of dental implantology and orthopedic and surgical repair and replacement, numerous implant materials have been used with varying degrees of success. Metallic implants and prostheses, for example, have been found to have drawbacks due to chemical and electrolytic reactions, body rejection, toxic response, metal fatigue and failure, interference with healing, and inability to bond with bone. More recently, ceramics and polymers have been used with improved results insofar as bodily reaction is concerned, but problems still remain in developing permanent fibrous connective tissue and/or bony attachment (fixation) at the implant site.

Providing an implant with a porous surface at its interface with bone or other tissue has been recognized as promoting a firm union between the implant and the adjacent membrane in which it is embedded. For example, U.S. Pat. No. 3,628,248 issued Dec. 21, 1971 to E. A. Kroder et al. describes a procedure for preparing a tooth root replica implant from a mixture of polymethyl methacrylate beads and potassium chloride granules in a weight ratio of approximately 4:1. The powder mixture is combined with liquid monomer and a small amount of benzoyl peroxide (to initiate polymerization) in a mold for self-curing. After removal from the mold, the root implant is placed in boiling water for about 1 minute to extract a portion of the potassium chloride, thereby producing porosity.

As pointed out, however, in U.S. Pat. No. 3,713,860, issued Jan. 30, 1973 to A. Auskern, residues of additives to methyl methacrylate monomer, such as inhibitor, catalyst, or promoter, may cause tissue reactions at the implant site, and the benzoyl peroxide initiator of Kroder is known to be toxic to human tissues. The Auskern patent discloses a porous ceramic aluminum oxide bone substitute that is impregnated with pure methyl methacrylate (MMA) monomer. The monomer is then polymerized by gamma radiation from a suitable source, such as cobalt-60. If not previously shaped to size, the plastic-reinforced ceramic body is then machined, and the areas where bone or tissue ingrowth is desired are exposed to a suitable solvent (e.g. acetone) in an ultrasonic bath for 15 to 30 minutes to dissolve the polymer plastic to a preferred depth in the range of 100 to 400 microns.

According to Auskern, connective and bone tissue will grow into the pores and be firmly bonded to the ceramic if the porosity of the ceramic is in the range of 30–50 percent by volume, with the greater number of pores being in the range of 75 to 150 microns in diameter. On the other hand, a paper published by the present applicant in The New York Journal of Dentistry, Vol. 42, No. 10, pp. 331–341, Dec. 1972, suggested that the optimum porosity size for attachment between the periosteum and a polymer plastic tooth implant might fall in the range of 150–450 microns.

Another investigator has suggested a prosthesis material useful for artificial bones or teeth in the form of a heat-consolidated body composed of an integrated mixture of discrete microcrystals of calcium phosphate and a refractory compound such as aluminum oxide (see U.S. Pat. No. 3,787,900 issued Jan. 29, 1974 to T. D. McGee). In using this material for dental implants, McGee suggests providing porosity for the base of the teeth, where they fit in the alveolar sockets, by adding a volatile material such as naphthalene crystals to the dry ingredients at the root end of the implant mold before pressing and firing. In one example, forty percent naphthalene crystals were incorporated into one half of a cylindrical specimen to produce 200–500 micron pores in one end after firing. The specimen was implanted into the jawbone of a dog. A very strong bond, believed to be mineralized bone, developed between the implant and the jaw after 10 weeks.

Considerable work on dental implant material comprising an acrylic polymer mixed with organic bone has been done by M. Hodosh. See, for example, U.S. Pat. Nos. 3,609,867 and 3,789,029. In the latter patent, Hodosh describes a process for obtaining increased porosity near the outer surface of the polymer implant, where such porosity is most beneficial, by adding a measured amount of N-tributyl phosphate (a blowing agent) to a mixture of polymethacrylate, grated bone, and a foaming agent. The total mixture is polymerized in a mold at 300° F. for 30 minutes. After removal from the mold, the processed implant has an outer skin that must be removed by suitable procedures, such as sand-blasting, to expose the porosity caused by the N-tributyl phosphate. According to Hodosh, when the prosthesis is implanted, tissues penetrate the pores to effect a secure fibrous interlock between the implant and the surrounding periodontal membrane. With such a blowing agent no predictable or standard pore size can be achieved, however.

Despite the progress in ceramic and polymer plastic implants and prostheses outlined above, there still exists a need for a plastic implant having standardized pore size (e.g., a desired hole, any dimension, uniformly distributed, every time) and with no toxicity. In addition, there is a need for a variety of porous plastic implant designs adapted for use in widely different jawbone configurations where no teeth exist (for example, narrow ridge implants, implants near maxillary sinuses, and implants in regions of inadequate alevolar height).

In particular, there is a need for a method of fabricating such an implant that can be performed quickly and easily by a dental or orthopedic surgeon or technician during an operating situation when the allowable time between the removal of a tooth or other surgical procedure and the fitting of the completed implant is measured in minutes.

SUMMARY OF THE INVENTION

It is an object of the present invention to provide a simple method for duplicating any hard tissue in the body (i.e., bones, teeth or cartilage) and to permanently affix the implant to its adjacent tissues.

It is another object of the present invention to provide a simple method for fabricating a cast polymer plastic implant having that surface portion intended to be exposed to an endosseous or connective tissue environment formed with a predetermined optimal pore size for encouraging either osteogenesis or connective tissue ingrowth from the host bone or soft tissues into the implant material.

It is another object of the invention to provide a process for fabricating a polymethyl methacrylate implant structure without using any toxic additives, or any toxic or otherwise dangerous materials to create the desired degree, size and depth of implant porosity.

Another object of the invention is to provide a molded plastic structure in any desired shape by a procedure that is rapid simple and inexpensive, and that requires only the usual equipment available to a dental or orthopedic surgeon.

These and other objects are achieved by the method of the present invention, which provides a cast polymethyl methacrylate implant having an integrally cast exposed porous surface portion or portions with a predetermined pore size or sizes in the range of from about 50 microns to about 400 microns and a controlled degree of porosity such that upon insertion into an implant site, such surface portions will be particularly and selectively receptive to the development of the desired type of fibrous connective attachment (e.g., either "soft" connective tissue or "hard" bony tissue) to the contiguous host tissue of the implant site.

For example, the method of the present invention will provide a tooth root implant having a predetermined porosity in the areas exposed to alveolar and gingival environments. The surface of the implant tooth root, whether the implant is a replica of an extracted root or is a preformed shape to suit the site of a missing tooth, should have a pore size specifically adapted to promote ingrowth and adhesion of periodontal membrane tissues in the portion within the jawbone socket and adapted to encourage ingrowth of soft tissue at and below the gum line.

On the other hand, implants intended to be inserted into direct contact with, or to replace, bony parts of the body should have a larger pore size (at least 150 microns) that has been found essential to promote hard bone cell ingrowth into the intraosseal portion of the implant.

Such an implant is prepared by adding a completely non-toxic, water soluble, crystalline material (e.g. sodium chloride or sugar) to a powdered acrylic polymer, the volume ratio of crystalline material to polymer being equal to the desired porosity of the finished implant. The particle size of the crystalline material, which preferably is sodium chloride, should be preselected to be the same as the desired pore size of the implant material.

It is important that the acrylic polymer have no added promoter or catalyst which could cause a toxic reaction at the implant site. The above mixture is then moistened to a suitable consistency with liquid monomer and poured into a mold that has been suitably prepared by a technique as described in detail below. The mixture may fill the mold or, alternatively, the mixture may be poured around a previously placed reinforcing member of metal, hard nonporous acrylic plastic, or other suitable material that may even include a processed natural root of a previously extracted tooth for which the implant is to be a replacement. Also, instead of having a reinforcing core, the mixture of salt and acrylic polymer-monomer can be reinforced by adding carbon fibers.

If the implant is intended to be a replacement for a tooth root, a pin of either hard plastic or metal may be incorporated in the mold for securing a subsequently placed tooth cap. Alternatively, the tooth crown portion may be molded integrally with the root by filling the top portion of the mold with pure acrylic polymer-monomer mixture to form a hard non-porous tooth crown portion.

After the mold is filled, the plastic mixture is polymerized by placing the mold flask in boiling water for a suitable time (usually about 10 minutes), as is well known in the art. The solidified implant is then removed from the mold.

During the polymerizing process a thin plastic skin forms over the portion composed of salt and plastic mixture, thereby sealing the salt crystals inside the surface. This skin must be removed, preferably by sandblasting, to expose the surface salt crystals. The salt is then leached out by placing the replica in boiling water again for about 4 to 15 minutes. This simultaneously sterilizes the replica, which is then ready for immediate insertion into the previously prepared implant site.

As indicated above, an important part of the method of the present invention is the proper preparation of the mold surface in those regions of the replica implant that are to have a porous surface. It has been found that without such preparation, the surface region of the polymerized salt-plastic mixture has a deficiency of salt crystals, thereby reducing or eliminating the porosity in the precise location where maximum porosity is desired. According to the method of the present invention, therefore, a preliminary coating of the leachable salt or sugar crystals is attached selectively to the portions of the mold surface prior to filling the mold with the plastic mixture.

The procedure for attaching the crystals to the mold surface may be accomplished by any one of several alternative methods that also include coating the mold with a conventional release agent to facilitate removing the finished replica from the mold. A well-known release agent used in dentistry is sold under the name "Mar-va-foil", but any similar preparation may be used instead.

Usually, a thin coating of the release agent alone will be applied to the entire inside surface of the mold, but in one method, salt crystals having a particle size equal to the desired pore size can be mixed with the release agent until it is saturated and the resulting mixture applied to those regions of the mold where a porous surface of the replica is desired. When the release agent dries, a dense layer of salt crystals will be attached to the selected portions of the mold surface. The mold is then ready for the plastic casting steps described previously.

In another method of mold preparation, the entire inner surface of the mold is coated with a release agent. An acetate cement, such as "Duco" brand sold by E.I. duPont de Nemours & Co. (Inc.), is thinned with a solvent such as acetone or methyl ethyl ketone to increase its flowability and is then painted over the release agent in the region where porosity is desired. Salt crystals of desired size are sprinkled onto the thinned glue while it is still tacky. When the cement dries, a dense coating of salt crystals of the desired size will be attached to the selected areas of the mold, ready for the plastic mixture to be cast.

Instead of mixing the salt in an acetate cement or premixing it in the release agent, the crystals can simply be sprinkled on the release agent (or on a cement coating on top of the release agent) immediately after it has been coated on the mold surface and while it is still tacky. This technique is particularly useful when the entire surface of the replica is to be porous.

Another method of attaching leachable crystals to the mold surface comprises coating the inside of the mold with mineral oil, preparing a saturated solution of sodium chloride in hot water, coating the oil layer with the saturated saline solution, and placing the mold in an oven to evaporate the water. It has been found that if salt crystals of the desired size are used to make the saline solution and if the solution is so saturated that crystals of that size remain undissolved, then the additional crystals formed when the water evaporates are also generally of that same size. Although the mechanism by which this occurs is not fully understood, it is believed that the excess crystals in the solution may serve as "models" for other crystals that precipitate from the solution as the water evaporate. Regardless of the reason, this method also results in a dense layer of salt crystals attached to the mineral oil coating, which acts as a release agent for the subsequently cast plastic mixture.

With any of the preceding mold preparation techniques, a cast polymethyl methacrylate implant can be prepared which has high surface porosity of a predetermined pore size for creating the most effective bond with the surrounding host tissues while permitting the interior portion of the replica body to be made with reduced porosity or even nonporous for increased strength, as required by a given implant application.

Further details regarding the replica implants and their method of fabrication will be provided in the following description of the preferred embodiments in conjunction with the accompanying drawings.

BRIEF DESCRIPTION OF THE DRAWINGS

FIG. 13 through 18 illustrate the steps of an alternate method of correcting for inadequate alveolar bone height, in which FIG. 13 shows a natural tooth in situ;

FIG. 14 shows the mandibular socket of FIG. 13 after extraction of the tooth;

FIG. 15 shows a combination drill and tap in position to prepare deeper, threaded tooth support socket;

FIG. 16 shows the drill/tap completing the new socket;

FIG. 17 shows the prepared threaded socket after the combination drill/tap has been backed out;

FIG. 18 shows a prefabricated threaded porous plastic tooth support post inserted into the prepared socket, ready to receive a hard plastic tooth crown;

FIG. 20 shows a threaded plastic type of tooth implant in situ with the tooth crown in place;

FIG. 21 is a side view in partial section of the threaded support post of the tooth implant of FIG. 20;

FIG. 22 is a bottom view of the threaded support post of FIG. 21;

FIGS. 23A, B, and C show prefabricated threaded root implants in a range of sizes to suit different bone ridge formations;

FIG. 27 is a side view of a blade-type implant for use in molar replacement;

FIG. 28 is an end view of the implant of FIG. 27;

FIG. 29 is a top view of the implant of FIG. 27;

FIG. 30 is a side view of a blade-type implant for use in regions where there is less bone available than for the implant of FIG. 27;

FIG. 31 is a side view of another blade-type implant for use in front tooth replacement;

FIG. 32 is a side view of a blade-type implant design for use in replacing an upper tooth near a maxillary sinus;

FIG. 33 is an end view of the implant of FIG. 32;

FIG. 34 is a bottom view of the implant of FIG. 32;

FIGS. 35A and 35B are progressively smaller-sized versions of the implant of FIG. 32 for use in smaller jaws with smaller maxillary sinuses;

FIG. 49 is a side elevation of a cast polymer composite joint prosthesis having a solid plastic ball joint head, a small pore porous plastic midbody, and a large pore porous plastic fixation pin;

FIG. 50 is an alternate embodiment of a composite plastic joint prosthesis having large bone ingrowth holes in the fixation pin;

FIG. 51 shows a joint prosthesis inserted in the adjoining end of a limb bone;

FIG. 52 shows a hard plastic ball for use as a condylar head in a joint prosthesis;

DESCRIPTION OF THE PREFERRED EMBODIMENTS

Figure 1:
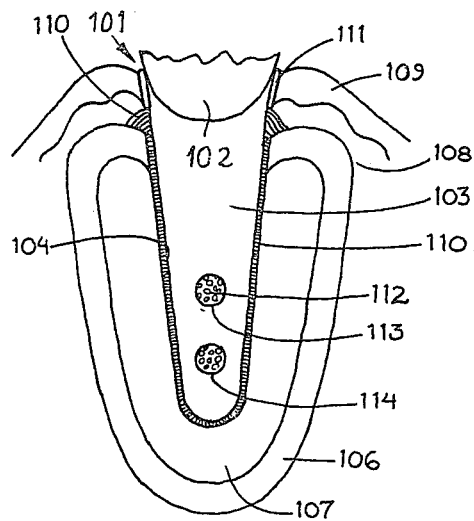
FIG. 1 is an enlarged side elevation of a composite hard plastic crown and porous plastic root tooth implant in a lower jaw of normal alveolar bone height, showing the mandibular bone in cross-section.

In the detailed discussion that follows, various applications of the invention to dental implant design will be described, followed by examples of bone implants and prosthetic devices, and concluding with a description of alternative methods for making the previously described implant structures and for emplacing them in the intended body location. In the drawings, the same or similar features will be identified by the same reference number in each figure for convenience.

The need for a tooth implant may arise from a variety of causes, and each situation may require a different implant structure. In addition, the type of tooth being replaced (e.g. molar, bicuspid or incisor) and its location in the mouth will affect the required shape of the implant support or root, both because each tooth encounters a different stress and because the alveolar ridge at the front of the mouth is normally narrower than at the rear. The location of the maxillary sinus cavities in the upper jaw may also affect the shape of the implant support. Consequently, the present invention contemplates a range of sizes, shapes, and constructions, as illustrated by the following drawings of tooth implant embodiments. All of the different designs incorporate, however, the underlying concept of pore size and porosity depending upon the type of tissue ingrowth that is desired.

FIGS. 1 through 5 illustrate several embodiments for use when replacing an existing tooth in a socket having normal alveolar bone height. In these drawings, as well as in all subsequent drawings representing in situ conditions, the anatomical details are rendered in a formalized schematic manner for simplicity.

Referring to FIG. 1, a plastic replica tooth implant 101 comprises a hard plastic tooth crown 102 integrally molded with a porous plastic tooth root 103. The term replica will be used to refer to a tooth implant or other plastic implant structure that has the exact size and shape of the tooth or bone that it replaces. Such a replica will normally be cast in a mold that has been prepared using the original tooth or bone as the model for the mold. In this case the tooth replica 101 has been set in an alveolar cavity 104 of the lower jawbone or mandible 105. The jawbone is composed of a cortical or outer bone portion 106 and an inner spongy medullary portion 107. The example of FIG. 1 illustrates a mandible having a normal alveolar height; i.e., the tooth socket extends well up near the top of the root portion of the implant. Above the jawbone lies the dermis 108 with the outer covering of the gums or gingiva 109 extending up to the top of the porous root portion of the implant.

FIG. 1 illustrates the situation after the implant has become fully attached to the alveolar socket by means of a periodontal membrane 110 and to the gingiva by an epithelial attachment 111. In addition, hard bone ingrowth 112 has occurred through two holes 113 and 114 drilled in the root portion of the replica, each hole being approximately 2 to 3 millimeters in diameter. Finally, fibrous tissue ingrowth 115, that constitutes an extension of the periodontal membrane, has occurred between the alveolar bone and the intermediate root portion of the tooth replica. As a consequence, the tooth implant is firmly attached both to the underlying jawbone and to the overlying gingiva in a manner completely simulating the environment of a natural healthy tooth.

Figure 2:
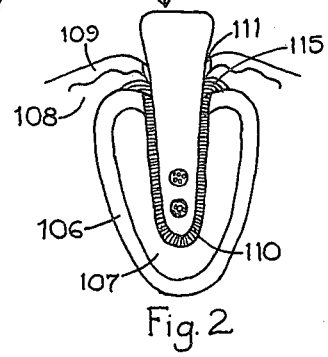
FIG. 2 is a view similar to FIG. 1 but showing a plastic tooth implant cemented into the alveolar bone socket.

FIG. 2 illustrates a replica 101 that is the same as the replica of FIG. 1. In this case the replica has been cemented into the alveolar cavity by a suitable cement, such as methyl polyacrylate (carboxylate) cement, glass-ceramic cement, or a cement known as Kodak 9-10 manufactured by the Eastman Kodak Company. In this embodiment the cement coating in the root portion of the replica provides an initial strong attachment to the jawbone, which is then supplemented over a period of weeks by ingrowth of periodontal tissue as described above.

Figure 3:
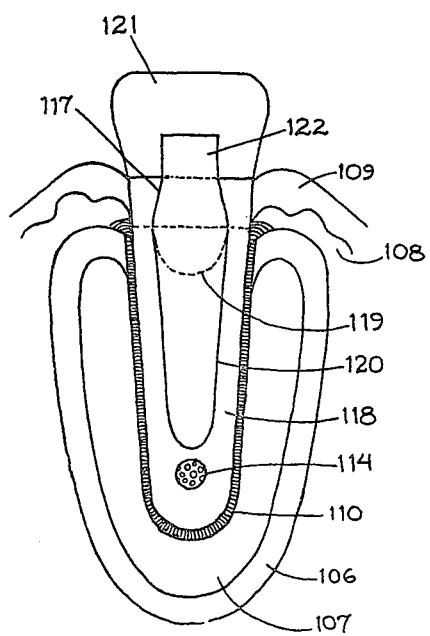
FIG. 3 is a view similar to FIG. 1 but showing an implant with a hard plastic core in a porous plastic root.

The next two FIGS., 3 and 4, illustrate two embodiments of a replica tooth implant formed by a two-stage technique. In these embodiments, the root portion is cast first and inserted in the alveolar socket. In the embodiment of FIG. 3 the root portion comprises a hard plastic insert 117 that extends, either partially or almost fully, to the bottom of the root and is surrounded by porous plastic 118 as illustrated. The possible range of lengths of the hard plastic insert 117 is shown between the dash line 119 and the solid line 120 on the drawing. After the root portion has been installed for a period of several weeks, so that connective tissue has had a chance to develop between the lower root and the alveolar socket and between the gingiva and the upper root, a preformed acrylic crown 121 can be attached to the upper portion 122 of the hard plastic insert that extends above the porous plastic root by any conventional cementing technique. In this way the implant support or root is protected by the adjacent teeth against the normal stresses exerted on a tooth crown during the critical period while the attachment membranes are forming between the root and the surrounding socket and gingiva. If desired, any conventional crown material other than acrylic, for example a porcelain jacket or acrylic veneers, can be used for the finished tooth.

Figure 4:
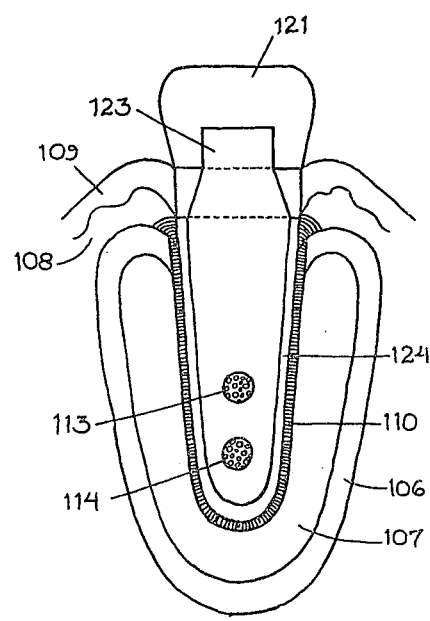
FIG. 4 is similar to FIG. 3 but showing an implant with a hard plastic root coated with porous plastic.

In FIG. 3, the hard plastic pin 122 provides reinforcement in the upper portion of what is primarily a porous plastic root. In the embodiment of FIG. 4, on the other hand, a hard plastic root replica 123 is coated with a relatively thin porous plastic outer covering 124 to provide a surface that will promote ingrowth of the periodontal membrane and the connective tissue at the gingival contact area. The embodiment of FIG. 4 is like the FIG. 3 embodiment in that the tooth crown 121 is cemented to the exposed mounting post of the hard plastic root 123 after the root has become fixed in the alveolar socket. This process normally takes only a few weeks at the most.

Figure 5A:
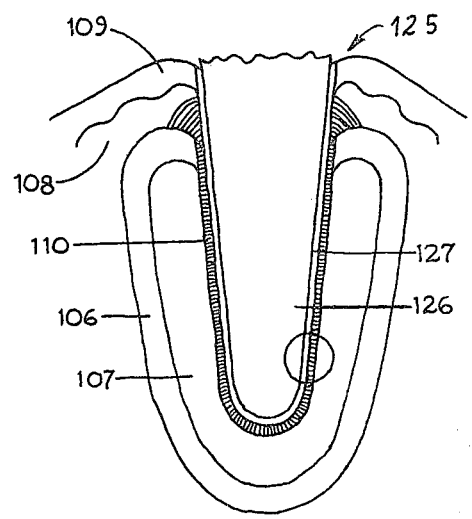
FIG. 5A is a view similar to FIG. 4 but showing a tooth implant formed from a natural extracted tooth with its root coated with porous plastic.
Figure 5B:
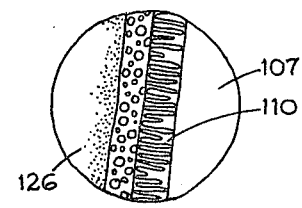
FIG. 5B is an enlarged view of the alveolar environment within the circle of FIG. 5A.

Occasionally in cases of gum disease, a sound natural tooth will become loose in its socket. In such a situation, it may be possible to use the tooth itself as the base for a dental implant. FIGS. 5A and 5B show a natural tooth 125 that has been extracted, the root portion 126 etched with phosphoric acid, a thin coating 127 of porous plastic applied to the root portion, and the tooth reinserted in its socket. When this procedure is accompanied and followed by the proper treatment for alleviating the underlying problems of the gum disease, the result is a recreation of the necessary periodontal membrane ingrowth in the lower root portion and epithelial attachment of the gingiva with the upper portion of the porous plastic coating to produce firm fixation of the tooth in its socket and a return to normal and healthy periodontal conditions.

As stated above, the tooth implant embodiment of FIGS. 1 and 2 is formed as an exact replica of a natural tooth by using the latter, immediately following extraction, as a pattern for a plaster mold fashioned by conventional flasking techniques. After the mold has set, the root portion is filled with a flowable mixture of acrylic plastic and leachable crystals of predetermined size. The crown portion of the mold is then filled with pure acrylic polymer/monomer mixture and the entire flask placed in boiling water until the replica casting has hardened. The cast replica is then removed from the mold and the crystals leached from the root, thereby creating the desired porosity. The details of this procedure are described in the final portion of the specification.

The two-step procedure for the implant of FIG. 3 differs from the one-step implants above in that a plaster mold of only the root of the extracted tooth is made in the first step. A hard (solid) plastic pin is placed in the mold before filling the remainder with the mixture of plastic and leachable crystals. The lower end of the pin serves to reinforce the root structure, while the upper end extends above the root to act as a mounting post for the preformed crown that is installed in the second step of the procedure.

In making the embodiment of FIG. 5A, the tooth root, after it has been etched with phosphoric acid, is coated with wax and then pressed back into its socket. In this way, the wax coating takes an exact snug impression of the tooth socket. Then the plaster mold is made in the usual way. The tooth is removed from the mold, dipped in boiling water to remove the wax, and replaced in the mold. The space previously occupied by the wax is then filled with a mixture of polymer, monomer, and leachable crystals, which is then processed to form the porous plastic coating. Instead of, or in addition to, premixing the leachable crystals with the polymer-monomer mixture, the crystals can be attached to the interior surface of the mold before the mixture is added, thereby increasing the porosity at the surface.

The embodiment of FIG. 4 is made in the same way as that of FIG. 5A except that the etched root of the natural tooth may be used as a pattern to make a hard plastic replica, formed with a crown mounting post at the top, that becomes the core of the implant. Alternatively, the hard plastic core may be selected from an assortment of prefabricated root shapes and sizes. This embodiment provides a structural strength comparable to the natural tooth by using a maximum amount of hard plastic in the root portion, and can be used when the natural tooth is not suitable (because of decay, fracture, or other defects).

Figure 6:
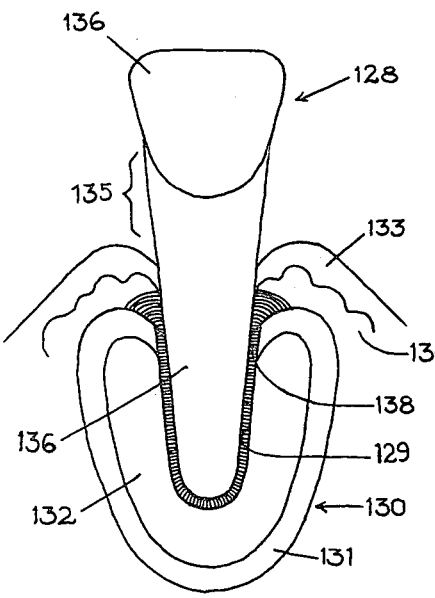
FIG. 6 is an enlarged side elevation of a natural mandibular tooth in a jaw having inadequate alveolar bone height.

Turning next to FIGS. 6 through 9, these figures illustrate various implant tecnniques and embodiments for use in situations where the alveolar height is abnormally low. FIG. 6 depicts a natural tooth 128 in situ in the alveolar cavity 129 of a mandible 130, having cortical bone portion 131 and inner spongy bone portion 132. In FIG. 6 the height of the alveolar bone is abnormally low, causing the gums (gingiva) 133 and the underlying dermis 134 to recede, thereby exposing intermediate root portion 135 between the tooth crown portion 136 and the lower root portion 137 that is held in the socket by periodontal membrane 138. This is an atrophied condition of the periodontal environment that causes gradual deterioration and ultimate loss of the natural tooth, followed by a strong tendency for alveolar resorption unless appropriate dental countermeasures are undertaken promptly.

Figure 7:
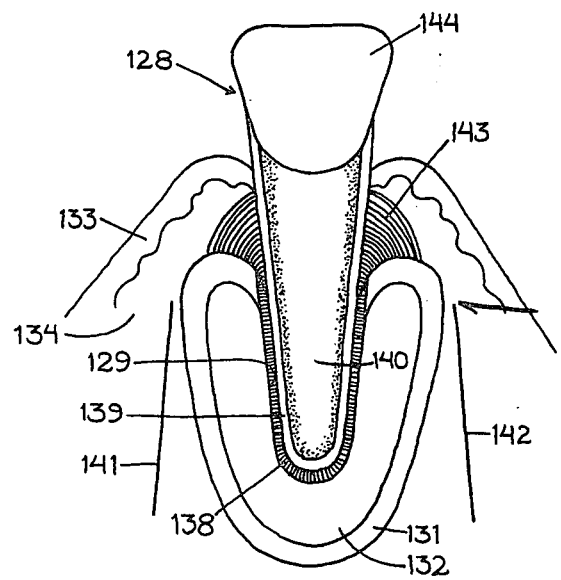
FIG. 7 is a view similar to FIG. 6 but showing the same tooth following extraction, coating of the root with porous plastic, reinsertion, and subsequent stimulation of connective tissue ingrowth to create a normal alveolar height.
Figure 8:
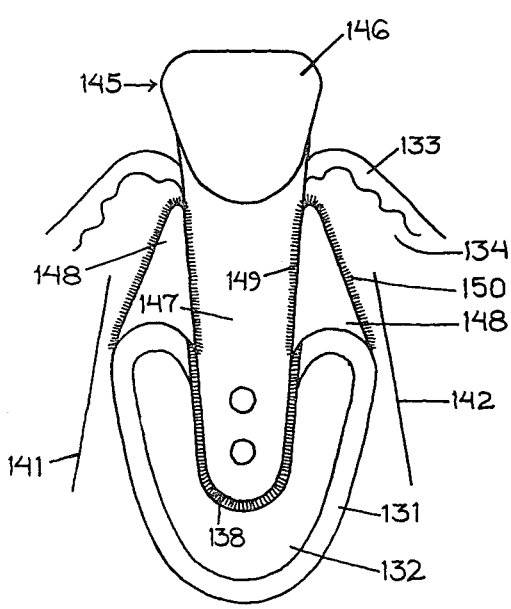
FIG. 8 is a view similar to FIG. 7 but showing a plastic replica tooth implant having a hard plastic crown and porous plastic root set into a built-up alveolar ridge of synthetic bone.

Assuming that the atrophy of the jawbone and resulting damage to the natural tooth has progressed to the point where extraction of the tooth is required, FIGS. 7-9 illustrate three approaches to the problem of rebuilding the alveolar ridge and fixating a replacement tooth. In FIG. 7, the natural tooth has been removed, treated in exactly the same way as the embodiment of FIG. 5, and replaced in its socket. The porous plastic coating 139 is strongly bonded to the etched root 140 and, in turn, provides a superior surface for encouraging the ingrowth of periodontal membrane cells in the alveolar socket.

At the time that the tooth is extracted, the dermis is also undercut along each side of the jawbone, as indicated by lines 141 and 142. Then after the treated tooth has been replaced in its socket, the dermis and overlying gingiva are pulled up to the normal gum line of the tooth and sutured in place. Within a few weeks, new periodontal membrane tissue 143 will grow upward from the jawbone and attach firmly to the porous plastic surface on the previously exposed intermediate portion of the tooth root. Concurrently, the gingiva will form an epithelial attachment to the upper margin of the porous plastic coating. Thus, the reparative approach taken with this embodiment is to encourage the formation and attachment of fibrous connective tissue to the previously exposed root portion of the natural tooth. After a period of natural growth and adaptation, a desired normal gingival condition results, as shown by gingiva 132 disposed at the base of crown portion 144, with the root portion properly embedded in alveolar cavity 129 with fibrous connective attachments 138 in alveolar cavity 139 and new connective tissue 143 creating the effect of a normal alveolar ridge.

FIG. 8 shows an embodiment of a tooth implant 145, of the same type as that of FIG. 1, that has been inserted in alveolar cavity 129 to replace the natural tooth shown in FIG. 6. This embodiment is formed as an exact replica of the natural tooth by using the latter as a model for a plaster mold fashioned by conventional flasking techniques, just as described in connection with FIG. 6. Thus, replica embodiment 145 of FIG. 8 comprises a hard (i.e. solid) cast polymer crown 146 integrally formed with a porous plastic root portion 147. In this case, however, the alveolar ridge has been built up artificially at the time of inserting the implant by packing synthetic bone 148 around the exposed intermediate portion of the root.

The synthetic bone used to form the alveolar ridge in this and following examples preferably is composed of large pore cast porous polymer (e.g. polymethyl methacrylate) having pore sizes in the range of 200–400 microns. Other conventional synthetic bone materials can be used, however, such as porous ceramic titanium dioxide ($TiO_2$), glass ceramic, calcium phosphate ($Ca_3(PO_4)_2$), or biodegradable polymer (lactic acid).

After the dermis has been undercut and the gingiva pulled up and sutured in place, new connective tissue attachments 149 and 150 will occur between the implant and the synthetic alveolar ridge and between the synthetic ridge and the contiguous dermis, respectively.

Figure 9B:
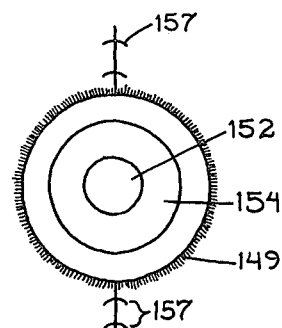
FIG. 9B is a top view of the embodiment of FIG. 9A.
Figure 9A:
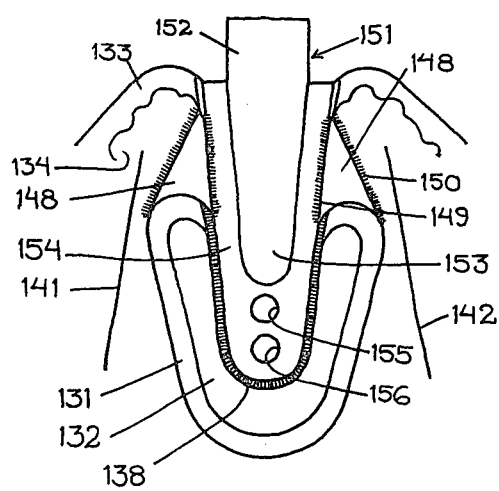
FIG. 9A is a view similar to FIG. 8 but showing a porous plastic tooth root implant having a hard plastic core.

Referring to FIGS. 9A and 9B, the two-step procedure described in connection with FIGS. 3 and 4 can also be used in the situation of inadequate alveolar height. The example of FIGS. 9A and 9B uses a replica root embodiment similar to that of FIG. 3, with a built-up alveolar ridge of synthetic bone, as in the example of FIG. 8. The replica root includes a solid plastic insert 151, having an exposed crown mounting post 152 and a reinforcing root portion 153 surrounded by a porous plastic jacket 154. Two holes 155 and 156 are provided for additional fixation by means of hard bone ingrowth.

As in the case of the one-step implant, the dermis is undercut and the gingiva pulled up around the upper margin of the porous plastic jacket, where it is held in place by sutures 157.

Figure 10:
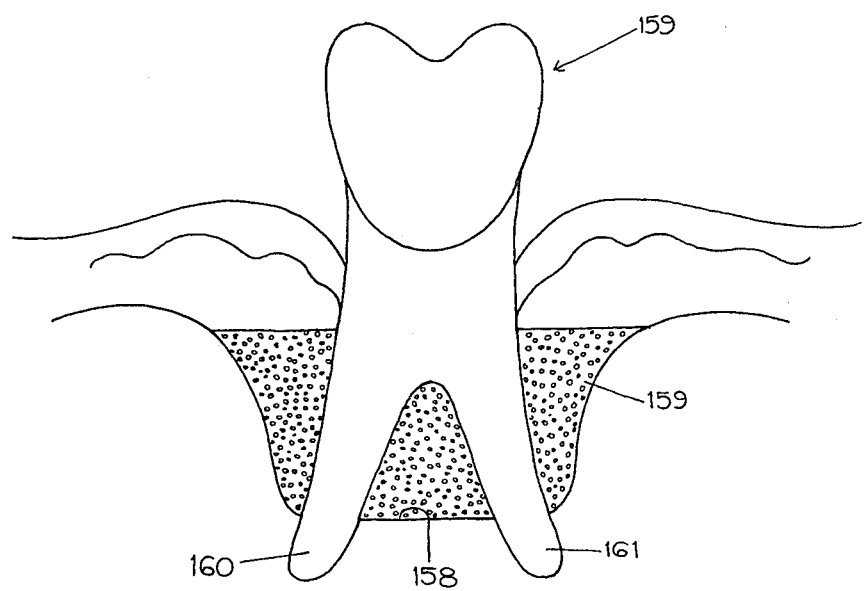
FIG. 10 is a side elevation of in situ replacement by porous plastic implant material of a bony periodontal defect in order to build up lost alveolar height.

In some cases, as shown by FIG. 10, alveolar bone resorption will create a trough 158 around the natural tooth 159. This situation can be treated in two ways. In the first procedure, porous synthetic bone material 159 (preferably polymethyl methacrylate with 200–400 micron pores) is packed around the intermediate portions of roots 160 and 161 to replace the lost alveolar bone. The second procedure is used when the tooth is loose and includes the additional steps of first extracting the tooth, etching the root, sealing the end of the root canal, and replacing the tooth in its socket before packing the synthetic bone material around it. The root etching procedure produces a roughened surface that promotes a good attachment to the periodontal membrane. If necessary, a porous plastic coating can be added, according to the previously described techniques. As in the procedures illustrated by FIGS. 7–9, the dermis should be undercut and the gingiva raised to the former gum line and sutured until connective tissue ingrowth has occurred.

Figure 12:
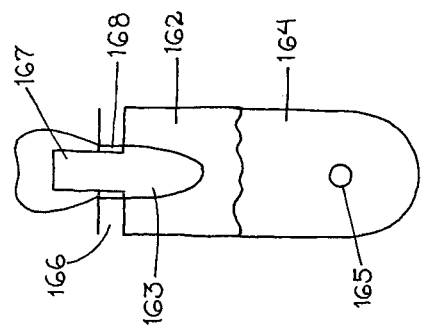
FIG. 12 is a cross section of FIG. 11 taken in the direction of arrows 12—12.
Figure 11:
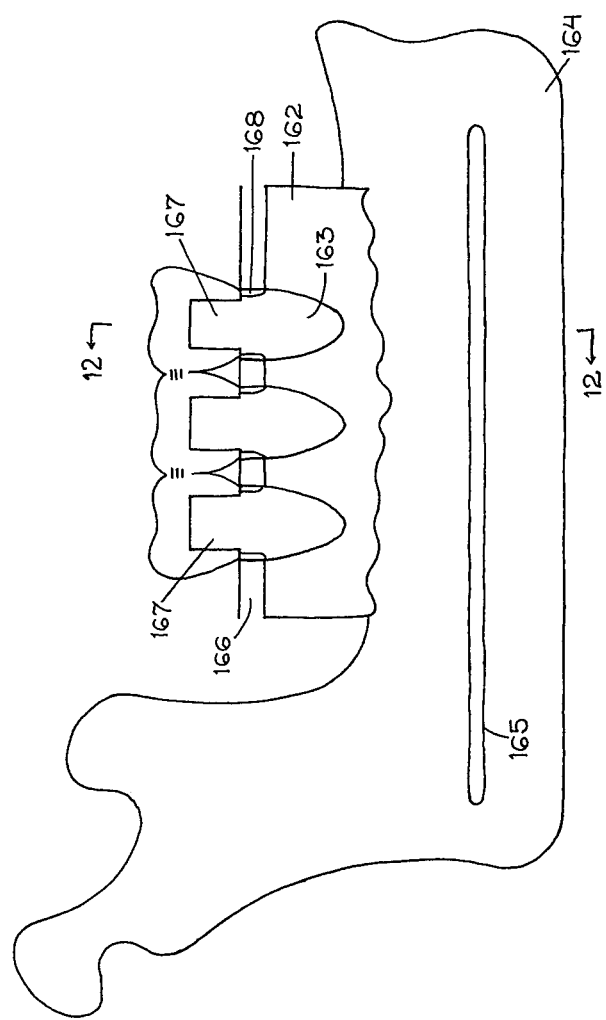
FIG. 11 is a side elevation of a multiple tooth replacement by means of a synthetic alveolar ridge implant in a lower jawbone.

The previous examples have all dealt with replacement of a single existing tooth by using the extracted tooth, either as a pattern for a cast plastic replica or, by suitable treatment, as its own replacement. FIGS. 11 and 12 illustrate a procedure for replacing a group of from two to five teeth by means of a multiple implant in two steps or stages. This procedure can be used both in the situation where all the replaced teeth are missing and there is very little alveolar bone height or where the group of teeth are all periodontally involved and must be removed.

In the first stage, an artificial alveolar ridge 162 of porous plastic is cast, using a wax impression or similar material as a pattern for a plaster mold by conventional techniques. Solid plastic inserts 163 may be cast integrally with the artificial ridge or may be cemented in place subsequently, as desired. The entire ridge structure is then placed in mating contact with mandible 164, (having alveolar canal 165) and the previously undercut gums 166 sutured in place around the inserts, leaving crown mounting posts 167 exposed.

Because the gingiva will not form an epithelial attachment with the smooth surface of the inserts, the exposed portions between the top of the artificial ridge and the base of the mounting posts should be covered with a suitable material 168 such as nylon velour or dacron mesh. Alternatively, these portions of the inserts 163 can be provided with porous surfaces (50–150 microns pore size) by the methods of this invention. Conversely, it should be mentioned that gingival attachment in any of the other described examples can be obtained through the use of nylon velour or dacron mesh, if desired.

After the implant has been in place for several weeks so that firm attachments have formed between the mandible and the large pore artificial ridge (hard bone ingrowth) and between the gingiva and the velour, mesh or small pore insert surface (soft tissue ingrowth), a one-piece group of solid plastic crowns 169 can be cemented onto the mounting posts. It will be appreciated, of course, that the crowns can be made of any other suitable conventional dental material and also that the artificial ridge can be made of any of the synthetic bone materials previously described. Furthermore, the artificial ridge building technique can be used alone without insert teeth to provide support for a denture.

Figure 13:
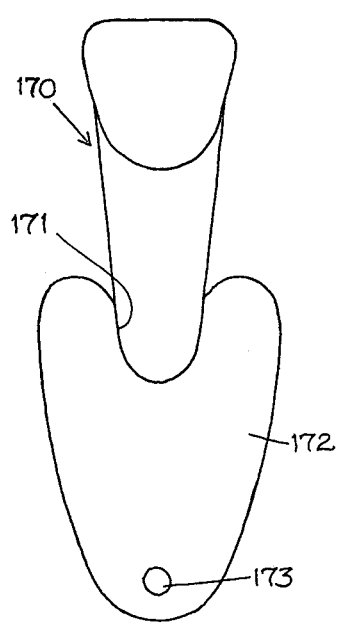
Figure 14:
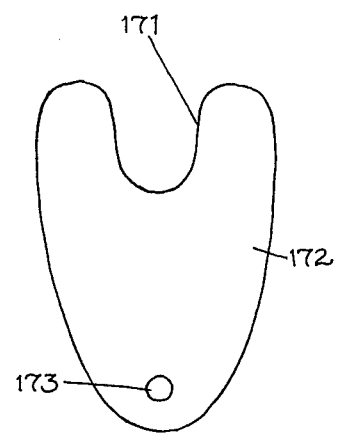
Figure 15:
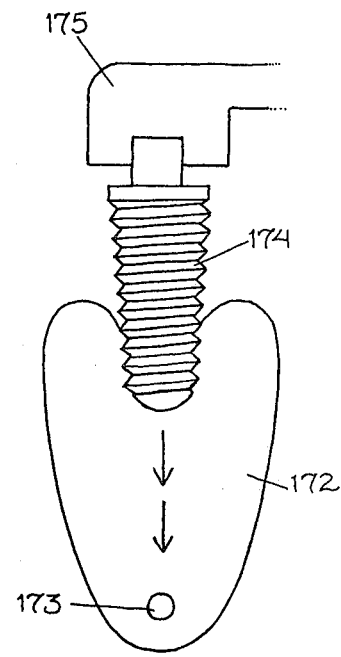
Figure 16:
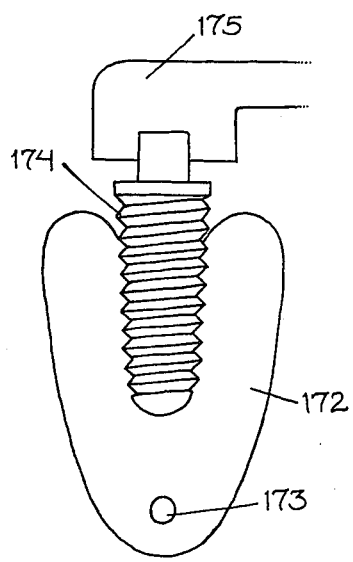
Figure 17:
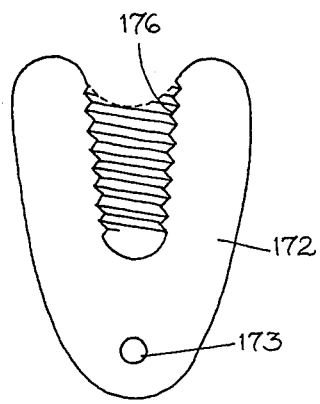
Figure 18:
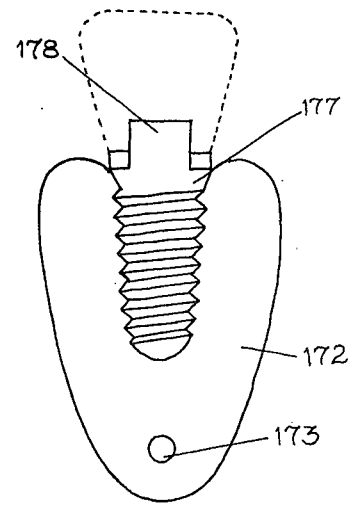

Instead of building up an artificial alveolar ridge to provide sufficient socket depth for proper support of implant teeth, the sockets themselves can be deepened by the procedure illustrated by FIGS. 13 through 17 and a prefabricated implant root installed as shown in FIG. 18. In FIG. 13, a natural tooth 170 is in an abnormally low alveolar socket 171 of a jawbone 172 having an alveolar canal 173. According to the illustrated procecure, the tooth is extracted (FIG. 14), and a combination drill and tap 174 mounted in a slow speed handpiece 175 is inserted into the alveolar socket (FIG. 15), run down to the desired depth (FIG. 16), and then backed out leaving a deepened, threaded socket 176 (FIG. 17). A mating threaded plastic insert 177 (FIG. 18) having a suitable porous surface is then threaded into the socket. The insert has a suitable crown mounting post 178 for subsequent attachment of a hard plastic crown 179 (shown in dashed lines).

Figure 19:
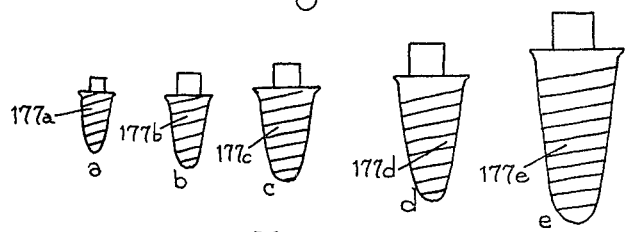
FIG. 19 shows a set of prefabricated threaded porous plastic tooth support posts in a graduated range of sizes for use in different regions of the mouth and in different sizes of jawbone.

Since the threaded plastic insert is sized to match the drilled and tapped hole, it is possible to provide an assortment of preselected insert sizes, as shown in FIG. 19, to correspond to similar sized taps for a full range of tooth and alveolar site sizes. The threaded inserts will simplify the job of preparing a tooth implant in many cases when there is an existing tooth as well as in those situations where the tooth is missing.

Additional embodiments of threaded porous plastic inserts are shown in FIGS. 20 through 23. In FIG. 20, a threaded insert 180 of porous plastic is shown in place in a jawbone 181 surmounted by dermis 182 and gingiva 183. A solid plastic crown 184 is cemented onto mounting post 185 at the top of the insert. If desired, the mounting post portion of the insert can be made of integrally molded solid plastic instead of porous plastic. Not only does this combination provide added strength but also the smooth surface of the solid plastic post will inhibit formation of epithelial attachment for the gingiva above the upper margin of the porous plastic cylindrical portions of the insert.

Features of this embodiment include a flared lip 186 at the top of the threaded portion that provides additional anchoring after the natural bone has grown in above it, as shown in FIG. 20. Another feature is an axial center hole 187 (best seen in FIGS. 21 and 22) that also produces improved anchorage by providing space for the ingrowth of hard bony cells and additional surface area for periodontal membrane attachment.

FIGS. 23A, B, and C illustrate a range of sizes for this type of implant in which the diameters vary inversely with length so that the surface area will remain approximately constant. Thus, the different sizes are adapted for use in different regions of the jaw, but all provide similar anchoring surface.

Figure 24:
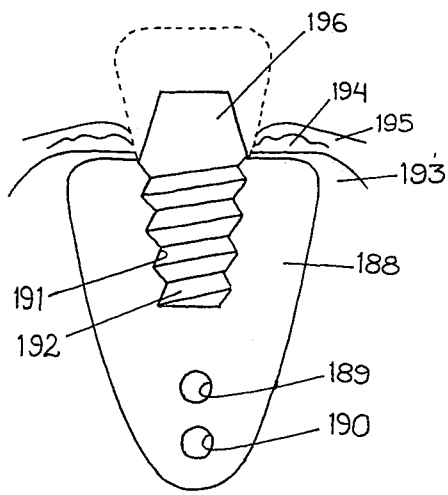
FIG. 24 is a side elevation of a hard-plastic screw post set in a porous plastic root implant for receiving a tooth cap.
Figure 25:
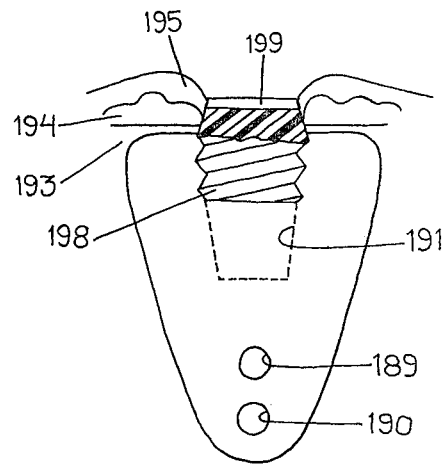
FIG. 25 shows a temporary screw plug fitted in the porous plastic root implant of FIG. 24.
Figure 26:
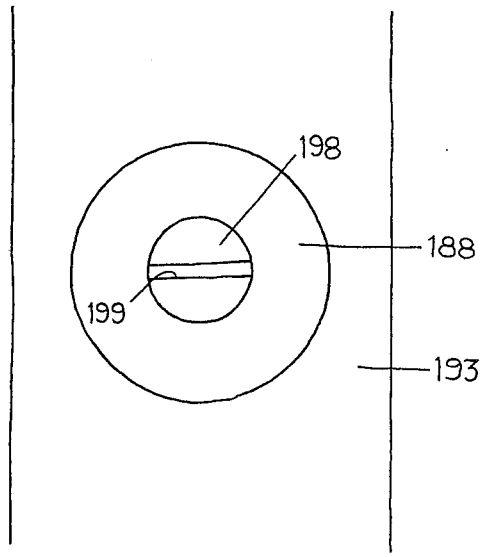
FIG. 26 is a top view of the implant of FIG. 25.
Figure 36:
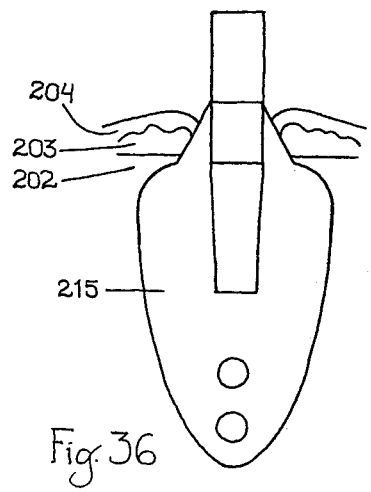
FIG. 36 is a side elevation of another form of blade-type tooth support implant.
Figure 37:
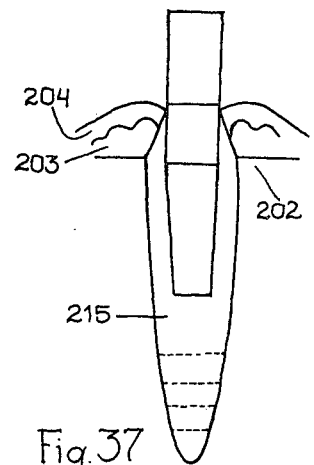
FIG. 37 is a front elevation of the implant of FIG. 36.
Figure 38:
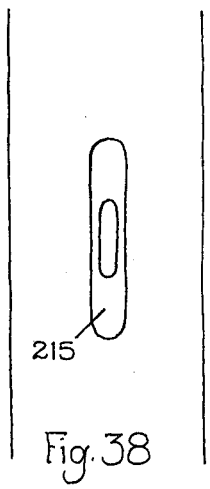
FIG. 38 is a top view of the implant of FIG. 36.
Figure 39:
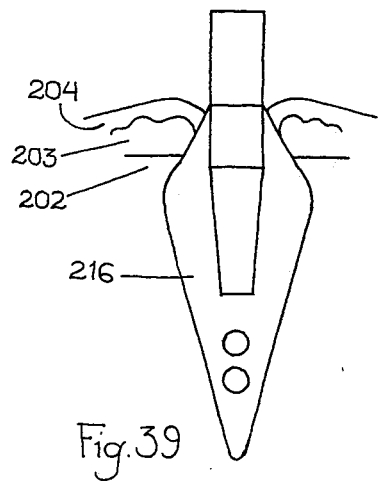
FIG. 39 is a side elevation of a conical form of tooth support implant.
Figure 40:
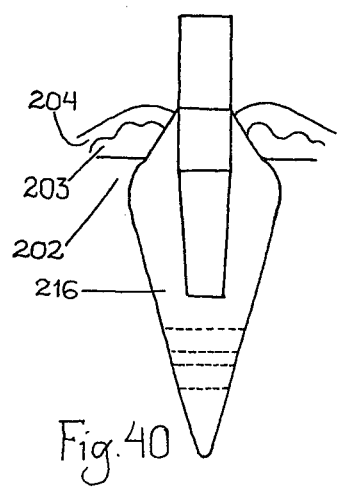
FIG. 40 is a front elevation of the implant of FIG. 39.
Figure 41:
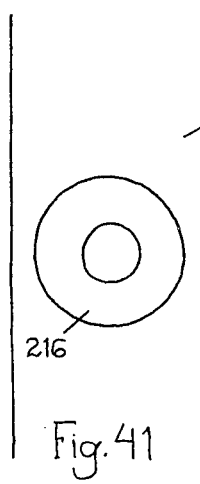
FIG. 41 is a top view of the implant of FIG. 39.
Figure 42:
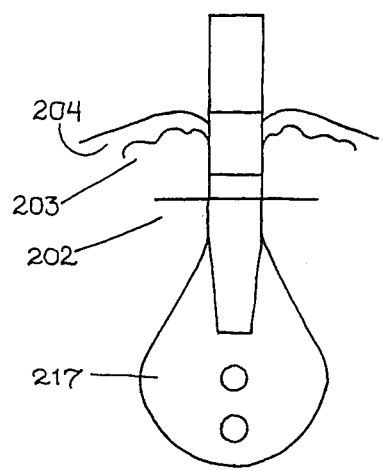
FIG. 42 is a side elevation of still another blade-type tooth support implant having a flared lower portion.
Figure 43:
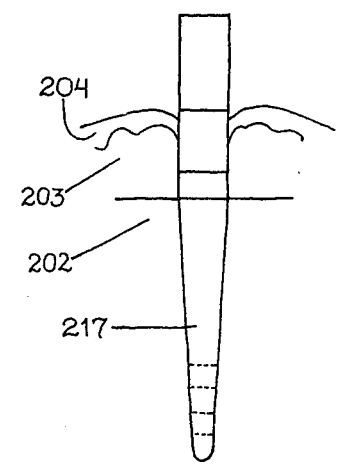
FIG. 43 is an end view of the tooth support implant of FIG. 42.
Figure 44:
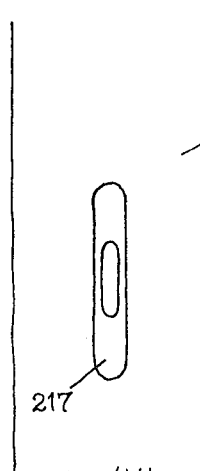
FIG. 44 is a top view of the tooth support implant of FIG. 42.
Figure 45:
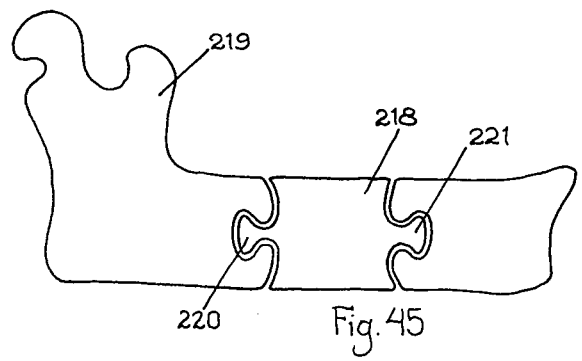
FIG. 45 is a side view of a lower jawbone having a diseased or otherwise defective section replaced by an interlocking porous plastic implant.
Figures 46A, 46B:
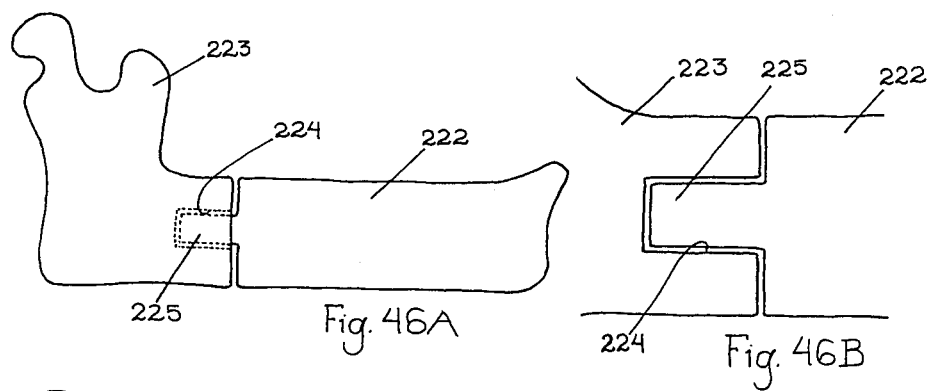
FIG. 46A is a side view of a lower jawbone of which a major portion has been replaced by a replica plastic implant.
FIG. 46B is an enlarged sectional view of the mortise and tenon joint between the host bone and the implant of FIG. 45A.

In the embodiment of FIGS. 24 through 26, a tapered large pore porous plastic implant 188 having two transverse bone anchoring holes 189 and 190 is provided with a tapered threaded hole 191 for receiving a mating threaded hard plastic mounting post support 192. Insert 188 is set into alveolar bone 193 so that its top surface is slightly below the top of the alveolar ridge, thereby encouraging the natural bone to grow over the implant, firmly locking it in place. The threaded plastic insert is cemented in the threaded hole with its mounting post 196 extending above the gingiva to receive a crown 197 (shown in dashed lines) after the implant has become securely attached to the jawbone by hard bony ingrowth. Alternatively, the implant can be made of small pore (50–150 micron) porous plastic. In that case, it will become attached to the jawbone by means of a softer periodontal membrame, which provides a shock absorbing medium.

In situations where there are no neighboring teeth to shield the mounting post during the period that the implant is becoming attached to the host bone, a temporary hard plastic or metal plug 198 having a top slot 199 can be screwed into the threaded hole, with its top surface flush with or below the surrounding gingiva 195. After the implant is set, the plug is removed and the permanent insert screwed in and cemented in place.

The porous plastic material used with the present invention is also suitable for making blade-type implants, and FIGS. 27 through 44 illustrate a number of different embodiments. In FIGS. 27-29 a wide-blade implant 200 of small pore plastic has an integrally cast solid plastic mounting post insert 201. The implant site is prepared by cutting a thin slot in the jawbone 202 deep enough so that the top of the implant blade will be below the top of the alveolar ridge. Dermis 203 and givgiva 204 are then sutured snugly against the tapered collar 205 to allow the gingiva to become attached to its porous surface. Subsequently, a crown 206 (shown in dashed lines) can be cemented onto mounting post 207.

Blade-type implant 200 has four bone ingrowth holes 208 and is particularly suited by shape and size for use in the rear of the lower jaw. Smaller and narrower blade type implants 209 (FIG. 30) and 210 (FIG. 31) are suitable for bicuspid and incisor supports, respectively.

In the upper jaw (maxilla), the presence of the maxillary sinus cavities create a problem in finding sufficient bone to support a tooth implant. This problem is solved by the curved-blade designs of FIGS. 32–34, in which a blade-type implant 211 has a curved inner edge 212 to conform the the curve of a maxillary sinus cavity 213. This type of implant can also come in a range of sizes as shown by implants 214 and 214B of FIGS. 35A and 35B, respectively.

Still further implant shapes for crown mounting post supports are shown in FIGS. 36 through 44. Implant 215 (FIGS. 36–38) has an arrowhead shape, implant 216 (FIGS. 39–41) has a conical shape, and implant 217 (FIGS. 42–44) has a fishtail shape.

As mentioned earlier, the same porous plastic implant material used for tooth implants can also be used for bone implants, bone replacement, and joint prostheses. The primary difference is in pore size, since hard bony ingrowth requires pore sizes of at least 200–400 microns. Referring to FIGS. 45-48, there are shown various techniques for mandibular repair that are equally useful for bone repair in other parts of the body. In FIG. 5 a porous plastic mandibular replacement section 218 is locked into mandible 219 by dovetails 220 and 221. It will be appreciated that the dovetail joints are actually a relatively tight fit and additionally may be cemented in place for adequate fixation until bone ingrowth can occur.

Figure 47:
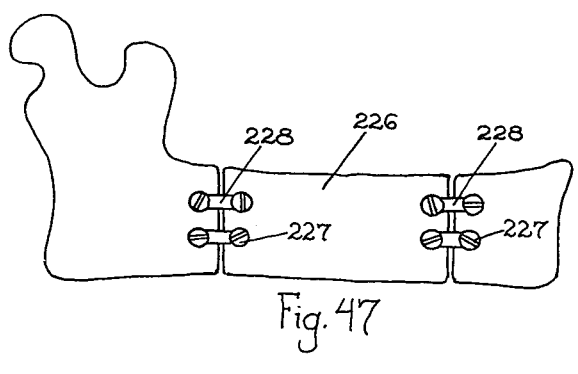
FIG. 47 illustrates an alternative form of attachment of a plastic mandibular defect replacement to the host bone by means of acrylic screws and plates.
Figure 48:
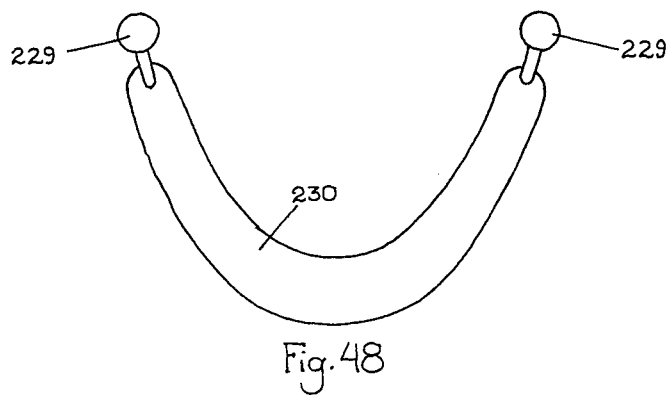
FIG. 48 is a top view of a mandible having plastic condylar head implants at each hinge joint.

A larger mandibular segment 222 (FIGS. 46A and B) is joined to the host hinge bone section 223 by a mortise and tenon 224 and 225. As before, the joint can be cemented for stabilization until bone ingrowth takes place. In FIG. 47 a bone insert 226 is held in place by acrylic screws 227 through acrylic plates 228 and also by cement, if desired. In FIG. 48 plastic condylar heads 229 have been implanted at each hinge of mandible 230.

The polymethyl methacrylate material described herein is also useful for making hip joint or other joint prostheses. In FIG. 49, a prosthesis of conventional form has a hard, solid plastic head 231, a small pore (50–150 microns) plastic midbody 232, and a large pore (200–400 microns) plastic fixation pin 233. The small pore midbody provides a surface for ligament attachment, and the large pore pin provides a surface for hard bony attachment when the pin is inserted in the end of a leg bone 234, for example (see FIG. 51). An alternate joint prosthesis of conventional design is shown in FIG. 50 with a smooth hard non-porous condylar head 235, a small pore midbody 236 and a large pore fixation pin 237 having large bone ingrowth holes 238. In FIG. 52 a hard plastic ball 239 has a porous plastic cover 240.

It should be understood that in referring to porous plastic portions, whether small pore or large pore, the porosity can either extend all the way through the portion or be only in a surface layer, depending on the strength requirements of the implant or prosthesis.

An important aspect of the present invention lies in the selection of proper pore size for the desired type of tissue attachment, whether soft connective tissue or hard bony tissue. Since the desired attachment of the replica embodiments of FIGS. 1–9 is by relatively soft fibrous connective attachments 24 and 28, the pore size of the sheath portion is preselected in the range from about 50 microns to about 150 microns, while the degree of porosity is preferably in the range from about 50 percent to about 75 percent by volume.

In recent tests on rats conducted under the direction of the applicant, it has been discovered that the choice of pore size is critical in determining the type of cell ingrowth that will occur in porous polymethyl methacrylate (hereinafter called porous PMM) material. In these tests, two series of small samples of porous PMM having pore sizes predeominantly in the ranges 50–150 microns and 200–400 microns, respectively, were implanted in rats in four different site environments; subcutaneous, intramuscular, intracerebral and intraosseous. The subcutaneous implants were retrived at intervals up to 70 days, but the implants in the other sites were kept in place a maximum of only 30 days.

In each of the three non-osseus sites the surrounding tissues were firmly attached to the implants of both pore sizes, but there was no evidence of either cartilage development (chondrogenesis) or bone development (osteogenesis) at any of the nonosseous implant sites. At none of the sites was any infection or any other pathological symptom noted. At the intraosseous sites, on the other hand, there was found in all cases a reparative bone formation adjacent to the implanted specimens. Within the pores of the materials, however, bone cells were found only in the large-pore (200–400 microns) specimens. In the small-pore (50–150 microns) specimens only soft tissue ingrowth was evident. These tests indicate, therefore, that the type of connection between bone and an intraosseous implant can be controlled by preselecting the pore size of the implant material in the regions of the implant surface that are contiguous to the host bone.

Referring again to the embodiment of FIGS. 1–9, therefore, by preselection the surface pore size of the entire root portion of the implant to be in the range from about 50 microns to about 150 microns, the growth of soft connective tissue into both the upper root surfaces and the intraosseal root surfaces can be assured.

The method of fabrication of the implant tooth replicas in each case is as follows:

(1) the natural tooth is extracted;

(2) the natural tooth is used, by well-known conventional dental laboratory techniques (e.g. by flasking) to form a replica mold;

(3) a conventional and well-known mold release agent is applied to the mold;

(4) a foundation for the porous portion of the replica root section is prepared by:
  (a) determining the desired porosity or porosity range, and degree of porosity.
  (b) selecting water soluble salt crystals having crystal sizes corresponding to the aforesaid pore sizes,
  (c) attaching a layer of said salt crystals to selected portions of said release agent coating on the inside of the mold,
  (d) mixing acrylic polymer and monomer with said salt composition in volume proportions corresponding to said desired degree of porosity to provide a molding composition of the required volume, (5) introducing said composition into the root portion of said mold;

(6) adding additional acrylic polymer and monomer to fill said mold, including said crown portion;

(7) heat polymerizing the ingredients in said mold, (8) extracting the casting from said mold;

(9) sandblasting or otherwise removing the surface skin from the root portion of the casting to expose the salt particles;

(10) boiling the casting in water for about four to fifteen minutes to leach out said salt to leave pores and voids in the place thereof; and

(11) pressing said porous casting into the extraction socket formerly occupied by the natural tooth.

The salt crystals may be any water soluble salt. Sodium chloride is preferred because of price and ease of removal, and especially because it is completely non-toxic and, in fact, residual amounts in the center portion of the root may benefit the healing process. On the other hand, any leachable crystaline material capable of more or less precise size classification may be used as long as it is non-toxic and has chemical compatibility with the plastic employed. The leaching medium may be other than water, likewise depending on its compatibility with the plastic and its non-toxicity.

Figure 53:
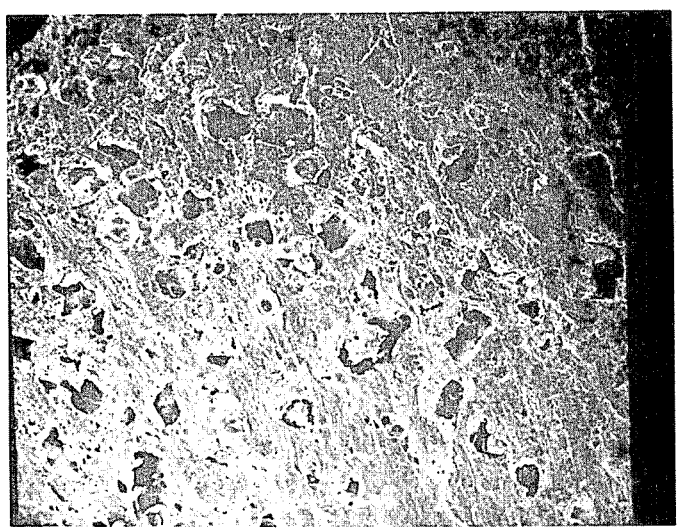
FIG. 53 is a photomicrograph at approximately 3× of a chlorine map of a sample of porous plastic having pore sizes of 100–150 microns.
Figure 54:
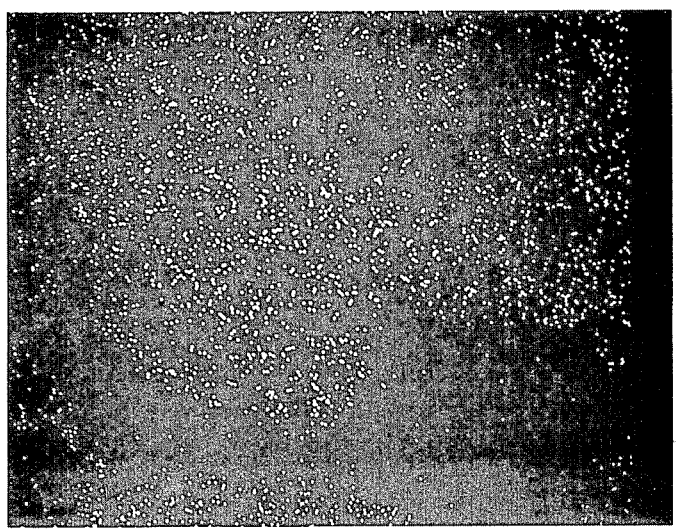
FIG. 54 is a photomicrograph at 40× of a sample of porous plastic having pore sizes of 75–150 microns.
Figure 55:
FIG. 55 is a photomicrograph at 25× of a sample of porous plastic having pore sizes of 300–400 microns.

As examples of the type of pores and porosity that are obtained by the above described casting techniques, microphotographs of samples of polymethyl methacrylate materials made with three different sizes of salt crystals are shown in FIGS. 53–55. FIG. 53 is a so-called chlorine scan at approximately 3× power of a sample of sodium chloride crystals having a size range of 100–150 microns. The photograph was made before leaching out the salt crystals, which show up as light spots on the dark background.

FIG. 54 shows a sample, after leaching, at 40× power that was made with salt crystals having a size range of about 75–150 microns. FIG. 55 shows a similar sample at 25× power that was made with salt crystals in the size range of 300–400 microns. All samples were made with equal volumes of salt crystals and polymer.

In view of polymethylmethacrylate's proven adaptibility for implants it is recognized as preferred for the instant invention at the present time. Recognizing, however, the rapid advance of scientific knowledge and expertise, it may well be a very short time that another, readily available, material may be used for the purposes of the present invention and perhaps even with greater advantage.

What is claimed is:

1. In the method of fabricating a plastic endosseous implant wherein a freshly extracted tooth is used as a master in preparing a replica mold corresponding to at least a root portion of said tooth, the improvement comprising the steps of:
  (a) attaching to the interior surface of the mold a dense layer of water soluble crystals of a particle size corresponding to a pore size desired in a surface region of the root portion of the implant,
  (b) mixing acrylic polymer and monomer with water-soluble crystals of a particle size corresponding to a pore size desired in a subsurface region of the root portion of the implant in volume portions to provide a preselected degree of porosity therein,
  (c) pouring such mixture in said mold,
  (d) curing the mixture in said mold to form a plastic replica corresponding to at least the root portion of said tooth,
  (e) removing the surface layer of plastic from the root portion to expose the water-soluble crystals, and
  (f) leaching said salt from said replica to produce porous surface and subsurface regions in at least the root portion of the tooth having predetermined pore size and porosity.

2. The method of claim 1 wherein said water-soluble crystals consist essentially of sodium chloride.

3. The method of fabricating a plastic endosseous implant comprising the steps of:
   (a) preparing a mold for an endosseous implant,
   (b) coating the mold interior with a release agent,
   (c) attaching to an interior surface of the mold a dense layer of water-soluble crystals of a particle size corresponding to a pore size desired in a surface region of the implant,
   (d) preparing a mixture consisting essentially of acrylic polymer and monomer with water-soluble crystals of substantially uniform size corresponding to a desired pore size in a subsurface region of said implant and in relative proportions corresponding to the degree of porosity desired therein;
   (e) introducing said mixture into the mold,
   (f) heat curing the material in said mold to form the implant,
   (g) removing said implant from said mold,
   (h) removing the sealing skin of the implant to expose the layer of water soluble salt crystals, and
   (i) leaching said water-soluble crystals from said implant.

4. The method of fabricating a plastic endosseous implant comprising the steps of:
   (a) preparing a replica mold of an endosseous implant site,
   (b) coating the mold interior with a release agent,
   (c) attaching to an interior surface of the mold a dense layer of water-soluble crystals of a particle size corresponding to a pore size desired in a surface region of the implant by painting the root portion of the mold with a layer of acetate cement and sprinkling said crystals on the cement while it is still tacky,
   (d) preparing a mixture of acrylic polymer and monomer with a water soluble salt of substantially uniform crystal size corresponding to the desired pore size in a subsurface region of said implant and in relative proportions corresponding to the degree of porosity desired therein,
   (e) introducing said mixture into the mold,
   (f) heat curing the material in said mold to form the implant,
   (g) removing said implant from said mold,
   (h) removing the sealing skin of the implant to expose the layer of water soluble salt crystals, and
   (i) leaching said salt from said replica.

5. The method of claim 4 wherein step (h) comprises peeling said layer of acetate cement from the surface of the replica.

6. The method of claim 4 wherein step (h) comprises sandblasting the exterior of the replica.

7. The method of fabricating a plastic endosseous implant comprising the steps of:
   (a) preparing a mold of an endosseous implant,
   (b) coating the mold interior with a release agent,
   (c) attaching to an interior surface of the mold a dense layer of water soluble crystals of a particle size corresponding to the pore size desired in a surface region of the implant,
   (d) preparing a mixture of essentially pure acrylic polymer and monomer with a water soluble salt of substantially uniform crystal size corresponding to a desired pore size in a subsurface region of said implant and in relative proportions corresponding to the degree of porosity desired therein,
   (e) introducing said mixture into the mold,
   (f) heat curing the material in said mold to form the replica,
   (g) removing said replica from said mold,
   (h) removing the sealing skin of the replica to expose the layer of water soluble salt crystals, and
   (i) leaching said salt from said replica, said leaching step being carried out in boiling water for about 4 to 15 minutes.

8. The method of fabricating a plastic tooth implant comprising the steps of:
   (a) preparing a replica mold corresponding to a tooth implant site, the mold having a root portion and a crown portion,
   (b) coating the mold interior with a release agent,
   (c) attaching to an interior surface of the mold a dense layer of water-soluble crystals of a particle size corresponding to the pore size desired in a surface region of the root porton of the implant,
   (d) preparing a mixture of acrylic polymer and monomer with a water-soluble salt of substantially uniform crystal size corresponding to the pore size desired in a subsurface region of said implant and in relative proportions corresponding to the degree of porosity desired therein,
   (e) introducing said mixture into the mold,
   (f) inserting a polymethylmethacrylate pin in said mold so as to extend partially into the root portion thereof and extend partially into the crown portion, said pin being dimensioned to be concealed wholly within said implant when cured,
   (g) adding acrylic polymer and monomer mixture to fill the rest of said mold,
   (h) heat curing the material in said mold to form the implant,
   (i) removing said implant from said mold,
   (j) removing the sealing skin of the implant to expose the layer of water soluble salt crystals, and
   (k) leaching said salt from said implant.

9. The method of fabricating a plastic tooth implant comprising the steps of:
   (a) preparing a replica mold corresponding to the shape of an extracted tooth, the mold having a root portion and a crown portion,
   (b) coating the mold interior with a release agent,
   (c) sprinkling on said coated interior surface of the mold a dense layer of water-soluble crystals of a particle size corresponding to the pore size desired in a surface region of the root portion of the implant,
   (d) inserting a polymethylmethacrylate pin in said mold so as to extend partially into the root portion thereof and extend partially into the crown portion, said pin being dimensioned to be concealed wholly within said replica when cured,
   (e) adding acrylic polymer and monomer mixture to fill the rest of said mold,
   (f) heat curing the material in said mold to form the replica,
   (g) removing said replica from said mold,
   (h) removing the sealing skin of the replica to expose the layer of water soluble salt crystals, and
   (i) leaching said salt from said replica.

10. In the method of fabricating a plastic endosseous implant wherein a freshly extracted tooth is used as a master in preparing a replica mold corresponding to at least the root portion of said tooth, the improvement comprising the steps of:

(a) attaching a layer of water-soluble crystals of a particle size corresponding to the pore size desired in the surface of the root portion of the implant to the interior surface of the mold, (b) mixing acrylic polymer and monomer with water-soluble crystals of a particle size corresponding to the pore size desired in the subsurface root portion of the implant in volume portions to provide a preselected degree of porosity therein, (c) pouring such mixture into said mold to form a plastic root portion replica corresponding to the root portion of said tooth, (d) curing the mixture in said mold to form a plastic root portion replica corresponding to the root portion of said tooth, (e) removing a surface layer of plastic from the root portion to expose said water-soluble crystals, (f) leaching said salt from said replica, (g) coating the plastic root portion with cement, and (h) inserting the root portion into the socket of the freshly extracted tooth before the cement hardens for providing initial fixation of the replica implant in the socket.

11. The method of claim 10 wherein the cement comprises methyl polyacrylate (carboxylate).

12. The method of claim 10 wherein the cement comprises a glass-ceramic cement.

13. The method of claim 3 wherein step (c) comprises sprinkling said crystals on the release agent before it hardens.

14. The method of claim 3 wherein step (c) comprises mixing said crystals with said release agent prior to step (b).

15. The method of claim 3 wherein step (c) comprises preparing a saturated aqueous solution of said crystals, coating the layer of release agent with said saturated solution, and heating the mold to evaporate the water from said aqueous solution.

16. The method of claim 15 wherein said release agent comprises mineral oil.

17. A method of installing a plastic endosseous implant in a bone of a living being comprising the steps of:
(a) forming a threaded hole in said bone and
(b) screwing a mating threaded implant portion consisting of pure polymethylmethacnylate into said hole, said implant portion having a porous surface over the entire area in contact with said threaded hole with pore size restricted to the range of about 200–400 microns and extending to a depth of at least 2 mm. for promoting hard bony ingrowth into said pores.

18. A method of installing a plastic endosseous implant in a bone of a living being comprising the steps of:
(a) forming a threaded hole in said bone and
(b) screwing a mating threaded implant portion consisting of pure polymethylmethacrylate into said hole, said implant portion having a porous surface over the entire area in contact with said threaded hole with pore size restricted to the range of about 50–150 microns and extending to depth of at least 2 mm. for promoting soft tissue ingrowth into said pores.

19. The method of claim 18 wherein the endosseous implant is a tooth crown support, said bone is a jawbone, and said porous surface extends up to the gum line for promoting gingival attachment to said implant.

20. The method of claim 19 wherein said threaded hole is formed by tapping a natural alveolar socket.

21. The method of claim 20 comprising deepening said natural alveolar socket to compensate for indadequate alveolar height.

22. The method of claim 2 wherein the mixture of step (b) consists essentially of a powdered acrylic polymer, a liquid acrylic monomer, and said sodium chloride crystals.

23. The method of claim 3 comprising the additional step, after step (e), of adding essentially pure acrylic polymer and monomer mixture to fill the rest of the mold.

24. The method of claim 3 wherein the water-soluble salt consists essentially of sodium chloride.

25. A method of implanting a replica tooth in an alveolar socket where the adjacent bone height is abnormally low, the method comprising the steps of:
undercutting the dermis along each side of the bone ridge adjacent to the alveolar socket;
inserting a replica tooth root portion into the alveolar socket, the tooth root portion having a porous surface extending up to the normal line of gingival attachment, the porous surface having pore sizes in the range of about 50 microns to about 150 microns and the porosity extending to a depth of at least two millimeters;
building up the alveolar ridge to normal height by packing porous synthetic bone around the tooth root portion at the time of inserting the implant;
pulling the dermis and overlying gingiva up to the normal gum line of the tooth root portion; and
suturing the dermis and gingiva in place.

26. The method of claim 25 wherein the porous symethtic bone has pore sizes predominantly in the range of approximately 200 microns to approximately 400 microns.

27. A method of implanting a plurality of adjacent teeth in an alveolar environment where the alveolar ridge is abnormally low, the method comprising the steps of
undercutting the dermis along the alveolar ridge at the location of a plurality of adjacent teeth to be implanted;
forming an artificial alveolar ridge of porous plastic to fit the natural bone at said location, said plastic having pore sizes predominantly in the range from approximately 200 microns to approximately 400 microns;
installing crown mounting posts for the plurality of adjacent teeth in the top of the artificial alveolar ridge;
providing porous surfaces at the bases of the crown mounting posts to promote epithelial tissue attachment of the surrounding gingiva;
placing the artificial alveolar ridge in mating contact with the natural alveolar bone at said location;
suturing the previously undercut gums in place around the bases of the crown mounting posts.

28. The method of claim 27 further comprising the step of attaching artificial tooth crowns onto said crown mounting posts after firm attachments have formed between the natural alveolar bone and the artificial ridge and between the gingiva and the bases of the crown mounting posts.

29. A method of correcting an abnormally low alveolar ridge adjacent to a natural tooth caused by periodontal disease comprising the steps of:

packing porous synthetic bone around the natural tooth to build up the alveolus surrounding the tooth to normal height;

pulling the dermis and gingiva up to the normal gum line of the tooth; and;

suturing the dermis and gingiva in place.

30. The method of claim 29 further comprising the preliminary step of:

undercutting the dermis along each side of the bone ridge adjacent to the tooth.

* * * * *